(12) United States Patent  
Shibata et al.

(10) Patent No.: US 10,351,528 B2  
(45) Date of Patent: Jul. 16, 2019

(54) TETRAFLUOROSULFANYLPYRIDINE

(71) Applicant: UBE INDUSTRIES, LTD., Yamaguchi (JP)

(72) Inventors: Norio Shibata, Aichi (JP); Kohei Matsuzaki, Aichi (JP); Norimichi Saito, Yamaguchi (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 0 days.

(21) Appl. No.: 15/778,959

(22) PCT Filed: Sep. 23, 2016

(86) PCT No.: PCT/JP2016/078000  
§ 371 (c)(1),  
(2) Date: May 24, 2018

(87) PCT Pub. No.: WO2017/090309  
PCT Pub. Date: Jan. 6, 2017

(65) Prior Publication Data  
US 2018/0339969 A1 Nov. 29, 2018

(30) Foreign Application Priority Data

Nov. 25, 2015 (JP) ................... 2015-229884

(51) Int. Cl.  
*C07D 213/70* (2006.01)  
*C07D 213/71* (2006.01)

(52) U.S. Cl.  
CPC ......... *C07D 213/70* (2013.01); *C07D 213/71* (2013.01)

(58) Field of Classification Search  
None  
See application file for complete search history.

(56) References Cited

FOREIGN PATENT DOCUMENTS

WO 2014/062221 4/2014

OTHER PUBLICATIONS

Kanishchev et al, Synthesis and Characterization of 2-Pyridylsulfur Pentafluorides, Angew. Chem. Int. Ed., vol. 54, No. 1, pp. 280-284, (Year: 2015).*  
International Search Report for PCT/JP2016/078000, dated Dec. 5, 2016, 2 pages.  
Kirsch et al., "Bis(4-nitrophenyl)tetrafluorosulfuranes: Synthesis, Isomerization and Structural Characterization", J. Am. Chem. Soc. 1999, 121, 11277-11280.  
Kirsch et al., "Liquid Crystals Based on Hypervalent Sulfur Fluorides: The trans-(Trifluoromethyl)tetrafluorosulfuranyl Group", Eur. J. Org. Chem., 2006, 1125-1131.  
Zhong et al., "Preparation and Characterization of Alkenyl Aryl Tetrafluoro-λ(6)-sulfanes", Angew. Chem. Int. Ed., 2014, 53, 526-529.  
Extended European Search report for application No. 16868258.1, dated Mar. 28, 2019, 6 pages.

* cited by examiner

*Primary Examiner* — Zinna Northington Davis  
(74) *Attorney, Agent, or Firm* — Adsero IP

(57) ABSTRACT

A compound having a $SF_4$ group on a pyridine ring is provided. Specifically, the compound is represented by the general formula (c):

[Chemical Formula 1]

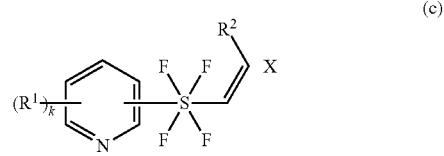

wherein k is 1 or 2; X is a hydrogen atom or a halogen atom; $R^1$ is a hydrogen atom, a halogen atom, a substituted or unsubstituted alkyl group having 1 to 18 carbon atoms, a substituted or unsubstituted aryl group having 6 to 30 carbon atoms, or a nitro group; and $R^2$ is a substituted or unsubstituted alkyl group having 1 to 18 carbon atoms or a substituted or unsubstituted aryl group having 6 to 30 carbon atoms.

6 Claims, No Drawings

TETRAFLUOROSULFANYLPYRIDINE

CROSS-REFERENCE TO RELATED APPLICATION

This application claims priority to and is a 35 U.S.C. § 371 national phase application of PCT/JP2016/078000 (WO2017/090309), filed on Sep. 23, 2016 entitled "TETRAFLUOROSULFANYLPYRIDINE", which application claims priority to and the benefit of Japanese Patent Application No. 229884/2015, filed Nov. 25, 2015, the disclosures of which are incorporated herein by reference in their entirety.

TECHNICAL FIELD

The present invention relates to tetrafluorosulfanylpyridines and a production method therefor.

BACKGROUND ART

Introduction of a fluorine substituent into a liquid crystal molecule, etc. is expected to improve dielectric anisotropy, etc., and attention is given to the development of electronic materials having a tetrafluorosulfanyl group (a $SF_4$ group), which exhibits particularly strong electron withdrawing properties, as a linker (Non Patent Literature 1). As a conventional method for constructing a $SF_4$ structure, a method in use of sulfide and fluorine ($F_2$) gas is known (Non Patent Literature 2). Also, in recent years, a method to synthesize a compound having a $SF_4$ group by radical addition of hlorotetrafluorosulfanylaryl to an unsaturated bond moiety is reported (Patent Literature 1 and Non Patent Literature 3).

CITATION LIST

Patent Literature

PTL 1: International Publication No. 2014/062221

Non Patent Literature

NPL 1: Eur. J. Org. Chem. 2006, 1125.
NPL 2: J. Am. Chem. Soc. 1999, 121, 11277.
NPL 3: Angew. Chem. Int. Ed. 2014, 53, 526.

SUMMARY OF INVENTION

Technical Problem

The methods of the above-described publications require fluorine gas, which is highly toxic and reactive, and chlorotetrafluorosulfanylaryl, the synthesis examples of which are limited. Accordingly, the synthesis and the use of a compound having a $SF_4$ structure are extremely limited. Although a compound obtained by introducing a $SF_4$ structure into a pyridine ring that is often used in physiologically active compounds in particular is expected to contribute to applications such as pharmaceutical and agricultural chemicals, the synthesis of such a compound is not achieved yet. In view of these circumstances, an object of the present invention is to provide a compound having a $SF_4$ group on a pyridine ring and a production method therefor.

Solution to Problem

The inventors found that the above object can be achieved by a specific halotetrafluorosulfanylpyridine, and accomplished the present invention. That is to say, the above-described object is achieved by the following present invention.

(1) A tetrafluorosulfanylpyridine represented by the general formula (c) below.

(2) The tetrafluorosulfanylpyridine as set forth in (1), wherein $R^1$ is a fluorine atom or a chlorine atom, and X is a chlorine atom.

(3) A tetrafluorosulfanylpyridine represented by the general formula (c') below.

(4) The tetrafluorosulfanylpyridine as set forth in (3), wherein $R^1$ is a fluorine atom or a chlorine atom, and X is a chlorine atom.

(5) A method for producing the tetrafluorosulfanylpyridine as set forth in (1), comprising the step of adding a radical species generated from a halotetrafluoropyridine represented by the general formula (a) below to an alkyne represented by the general formula (b) below to give a tetrafluorosulfanylpyridine represented by the general formula (c) below.

(6) A method for producing the tetrafluorosulfanylpyridine as set forth in (3), comprising the step of adding a radical species generated from a halotetrafluoropyridine represented by the general formula (a) below to an alkene represented by the general formula (b') below to give a tetrafluorosulfanylpyridine represented by the general formula (c') below.

Advantageous Effects of Invention

The present invention can provide tetrafluorosulfanylpyridines and a production method therefor.

DESCRIPTION OF EMBODIMENTS

Hereinafter, the present invention will be described in detail. In the present invention, the range "X to Y" includes the values at both ends, i.e., includes X and Y.

1. Tetrafluorosulfanylpyridine

A tetrafluorosulfanylpyridine of the present invention is represented by the general formula (c) or (c'). The compound represented by the general formula (c) may be also referred to as a vinyltetrafluorosulfanylpyridine, and the compound represented by the general formula (c') may be also referred to as an alkyltetrafluorosulfanylpyridine.

(1) Vinyltetrafluorosulfanylpyridine

A vinyltetrafluorosulfanylpyridine is represented by the general formula (c):

[Chemical Formula 1]

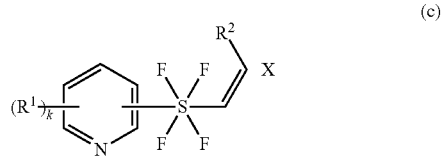

(c)

wherein k represents the number of $R^1$ and is 1 or 2.

$R^1$ is a substituent on the pyridine ring, and is a hydrogen atom, a halogen atom, a substituted or unsubstituted alkyl group having 1 to 18 carbon atoms, a substituted or unsubstituted aryl group having 6 to 30 carbon atoms, or a nitro group. In terms of the stability of source material chlorotetrafluorosulfanylpyridine, $R^1$ is preferably a halogen atom.

The halogen atom refers to a fluorine atom, a chlorine atom, a bromine atom, or an iodine atom.

$R^2$ is a substituent on the alkenyl group, and is a hydrogen atom, a halogen atom, a substituted or unsubstituted alkyl group having 1 to 18 carbon atoms, or a substituted or unsubstituted aryl group having 6 to 30 carbon atoms. From the viewpoint of the availability of the source material, $R^2$ is preferably a substituted or unsubstituted alkyl group having 1 to 18 carbon atoms or a substituted or unsubstituted aryl group having 6 to 30 carbon atoms. Examples of the substituent include a halogen, a nitro group, an alkoxyl group having 1 to 5 carbon atoms, and the like.

X is derived from the source material halotetrafluorosulfanyl compound, and is a hydrogen atom or a halogen atom. X is preferably a chlorine atom due to the ease of synthesis.

Specific examples are shown below.

[Chemical Formula 2]

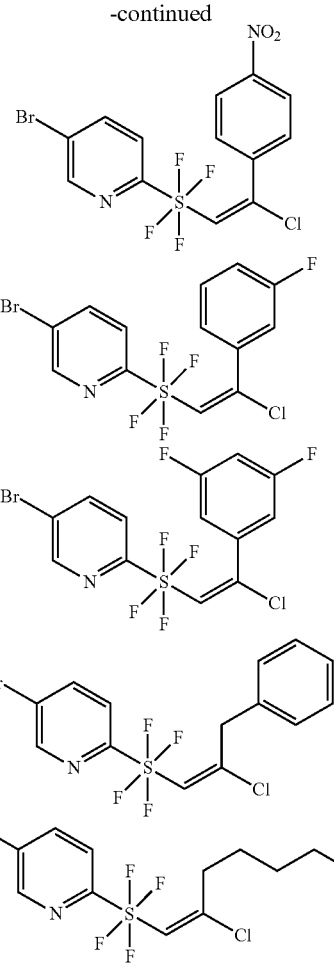

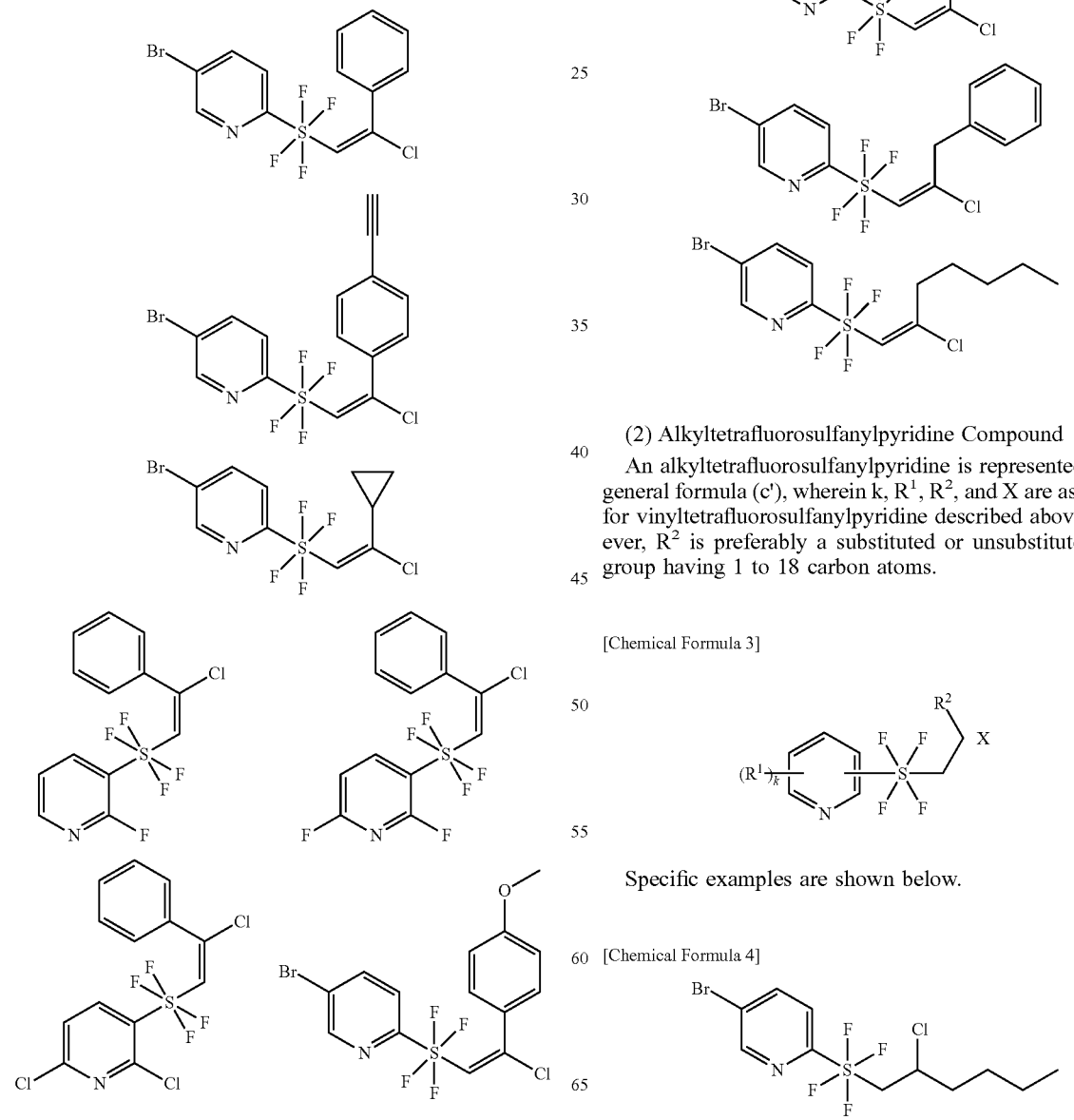

(2) Alkyltetrafluorosulfanylpyridine Compound

An alkyltetrafluorosulfanylpyridine is represented by the general formula (c'), wherein k, $R^1$, $R^2$, and X are as defined for vinyltetrafluorosulfanylpyridine described above. However, $R^2$ is preferably a substituted or unsubstituted alkyl group having 1 to 18 carbon atoms.

[Chemical Formula 3]

(c')

$$(R^1)_k \text{—pyridine—} SF_4\text{—}CH_2\text{—}CHR^2\text{—}X$$

Specific examples are shown below.

[Chemical Formula 4]

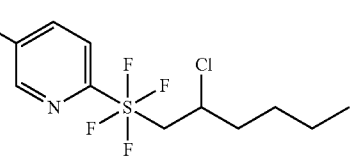

-continued

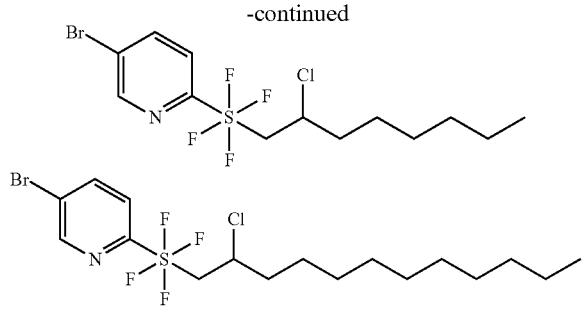

2. Method for Producing Tetrafluorosulfanylpyridine

It is preferable that the tetrafluorosulfanylpyridine is produced as follows.

(1) Method for Producing Vinyltetrafluorosulfanylpyridine (c)

As shown in the following scheme, a vinyltetrafluorosulfanylpyridine compound represented by the general formula (c) is produced by addition of a radical species generated from a halotetrafluoropyridine compound represented by formula (a) to an alkyne represented by formula (b).

[Chemical Formula 5]

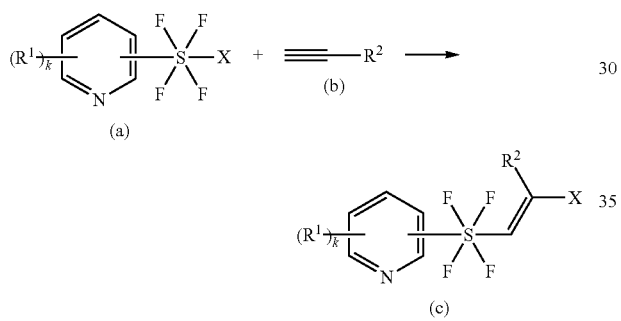

Specifically, an atom transfer radical addition reaction of a halotetrafluoropyridine (compound (a)) with an alkyne (compound (b)) is allowed to proceed in the presence of a radical initiator to give a vinyltetrafluorosulfanylpyridine (compound (c)). The amount of the radical initiator used is not limited, and is preferably 0.1 to 1.0 eq from the viewpoint of reduced cost. The amount of the alkyne used can be in excess relative to the pyridylsulfide compound, and is preferably 1 to 3 eq. The solvent is not limited but, in order to prevent degradation of the halotetrafluorosulfanylpyridine compound, is preferably a non-polar solvent such as hexane or pentane, an ether solvent such as diethyl ether or tetrahydrofuran, an aprotic polar solvent such as acetonitrile or nitromethane, or the like. The reaction temperature may be suitably adjusted, and is preferably −20 to 100° C.

The radical initiator usable in the present invention is not particularly limited as long as a radical is produced. Examples include benzoyl peroxide, tert-butyl peroxide, azobisisobutyronitrile, dimethyl 2,2'-azobisisobutyrate, trimethylborane, and triethylborane. Triethylborane is preferable in terms of availability.

(2) Method for Producing Alkyltetrafluorosulfanylpyridine (c')

As shown in the following scheme, an alkyltetrafluorosulfanylpyridine represented by the general formula (c') is produced by addition of a radical species generated from a halotetrafluoropyridine represented by formula (a) to an alkene represented by formula (b').

[Chemical Formula 6]

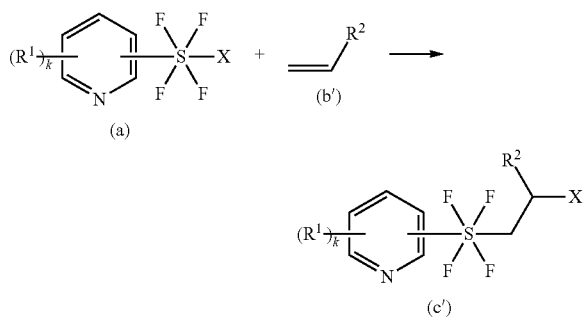

Specifically, an atom transfer radical addition reaction of a halotetrafluoropyridine (compound (a)) with an alkene (compound (b')) is allowed to proceed in the presence of a radical initiator to give an alkyltetrafluorosulfanylpyridine (compound (c')). The amount of the radical initiator used is not limited, and is preferably 0.1 to 1.0 eq from the viewpoint of reduced cost. The alkene can be used in excess relative to the pyridylsulfide compound, and is preferably in 1 to 3 eq. The solvent is not limited but, in order to prevent degradation of the halotetrafluorosulfanylpyridine compound, is preferably a non-polar solvent such as hexane or pentane, an ether solvent such as diethyl ether or tetrahydrofuran, an aprotic polar solvent such as acetonitrile or nitromethane, or the like. The reaction temperature may be suitably adjusted, and is preferably −20 to 100° C.

The radical initiator usable in the present invention is not particularly limited as long as a radical is produced. Examples include benzoyl peroxide, tert-butyl peroxide, azobisisobutyronitrile, dimethyl 2,2'-azobisisobutyrate, trimethylborane, and triethylborane. Triethylborane is preferable in terms of availability.

It is conjectured that this reaction is, but is not limited to, an atom transfer radical addition reaction shown below. That is to say, as shown in the following scheme, first, a halotetrafluorosulfanylpyridine as a starting material generates a radical active species (a') due to a radical initiator such as triethylborane. Then, an addition reaction occurs with a substrate (b) or (b') having an unsaturated bond moiety to give an alkyl radical intermediate. The resulting alkyl radical is considered to react with another molecule of (a) to give a tetrafluorosulfanylpyridine as an intended product.

[Chemical Formula 7]

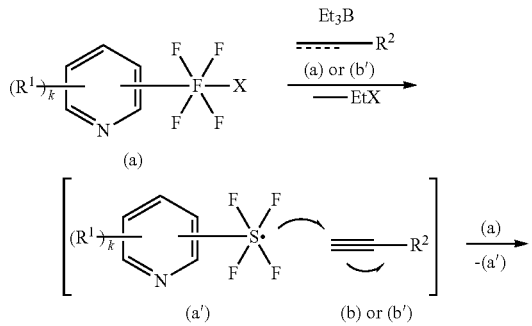

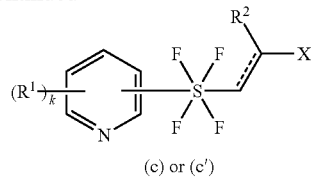

(c) or (c')

EXAMPLES

Example 1

The following reaction was performed to synthesize a vinyltetrafluorosulfanylpyridine compound (c).

[Chemical Formula 8]

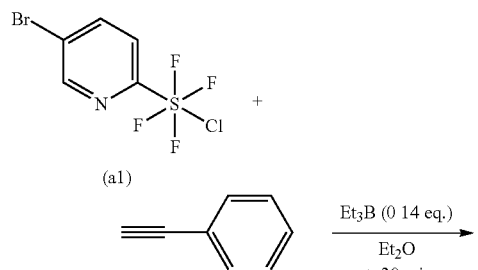

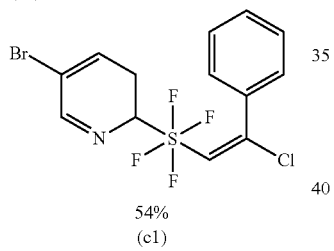

A 100 mL flask was charged with chlorotetrafluoropyridine (a1) (541 mg, 1.8 mmol) synthesized by the inventors, diethyl ether (4.5 mL), and ethynylbenzene (b1) (0.30 mL, 2.7 mmol, manufactured by Tokyo Chemical Industry Co., Ltd.) under a nitrogen atmosphere. Then, a triethylborane/hexane solution (0.26 mL, 1.0 M, manufactured by Sigma-Aldrich) was added to the mixture, and the mixture was stirred at room temperature for 30 minutes. After the end of the reaction, a saturated aqueous solution of sodium hydrogencarbonate was added, the product was extracted with dichloromethane, and the organic phase was dried over magnesium sulfate. Then, the solvent was distilled off under reduced pressure, and the mixture was purified by silica gel column chromatography (hexane/ethyl acetate=9/1, Rf value 0.5) to give product (c1) (392.3 mg, 54%) as a white solid.

Furthermore, the same synthesis was performed using the following compounds. The results of analyses by mass spectrometry and NMR are collectively shown below. In the present invention, mass spectrometry was performed with model LCMS-2020 manufactured by Shimadzu Corporation, and $^1$H-NMR and $^{19}$F-NMR were measured with Mercury 300 manufactured by Varian.

[Chemical Formula 9]

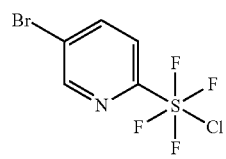 (a1)

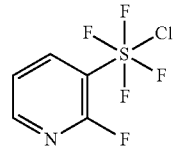 (a2)

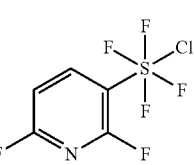 (a3)

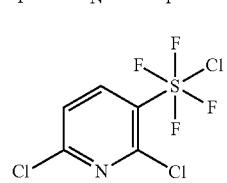 (a4)

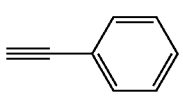 (b1)

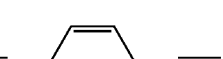 (b2)

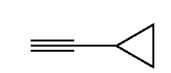 (b3)

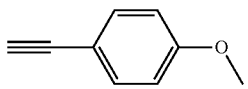 (b4)

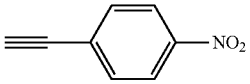 (b5)

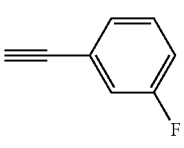 (b6)

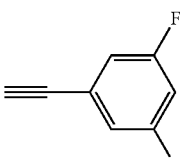 (b7)

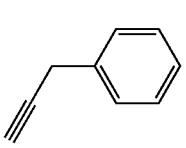 (b8)

(b9)

TABLE 1

| Example 1 | | |
|---|---|---|
| Source material | | Vinyltetrafluorosulfanylpyridine |
| a1 | b1 | (E)-5-Bromo-2-((2-chloro-2-phenylvinyl)tetrafluorosulfanyl)pyridine<br>c1 54% Yield<br>MS (EI, m/z) 401 (M+); $^1$H NMR (CDCl$_3$, 300 MHz): δ = 7.14-7.26 (m, 1H), 7.36-7.42 (m, 5H), 7.50 (d, J = 8.6 Hz, 1H), 7.89 (d, J = 8.6 Hz, 1H), 8.50 (s, 1H); $^{19}$F NMR (CDCl$_3$, 282 MHz): δ = −61.0 (d, J = 7.6 Hz, 4F) |
| a1 | b2 | (E)-5-Bromo-2-((2-chloro-2-(4-ethynylphenyl)vinyl)tetrafluorosulfanyl)pyridine<br>c2 44% Yield<br>MS (EI, m/z) 425 (M+); $^1$H NMR (CDCl$_3$, 300 MHz): δ = 3.13 (s, 1H), 7.20 (quint, J = 8.2 Hz, 1H), 7.39 (d, J = 7.8 Hz, 2H), 7.44-7.51 (m, 3H), 7.89 (d, J = 9.0 Hz), 8.50 (s, 1H); $^{19}$F NMR (CDCl$_3$, 282 MHz): δ = −61.1 (d, J = 8.2 Hz, 4F) |
| a1 | b3 | (E)-5-Bromo-2-((2-chloro-2-cyclopropylvinyl)tetrafluorosulfanyl)pyridine<br>c3 24% Yield<br>MS (EI, m/z) 365 (M+); $^1$H NMR (CDCl$_3$, 300 MHz): δ = 10.89-0.96 (m, 2H), 1.05-1.10 (m, 2H), 2.61-2.70 (m, 1H), 6.96 (quint, J = 9.0 Hz), 7.67 (d, J = 8.3 Hz), 7.98 (d, J = 8.3 Hz), 8.59 (s, 1H); $^{19}$F NMR (CDCl$_3$, 282 Hz): δ = −59.6 (d, J = 9.0 Hz, 4F) |

TABLE 1-continued

| Example 1 | | |
|---|---|---|
| Source material | | Vinyltetrafluorosulfanylpyridine |
| a2 | b1 | 3-(E)-2-Chloro-((2-phenylvinyl)tetrafluorosulfanyl)-2-fluoropyridine<br>c4 65% Yield<br>MS (EI, m/z) 341 (M+); $^1$H NMR (CDCl$_3$, 300 MHz): δ = 7.24-7.09 (m, 1H), 7.51-7.31 (br, 5H), 8.03 (t, J = 7.6 Hz, 1H), 8.27-8.15 (br, 1H); $^{19}$F NMR (CDCl$_3$, 282 MHz): δ = −63.1 (dquint, J = 21.9, 8.1 Hz, 1F), 72.3 (dd, J = 22.2, 8.3 Hz, 4F); $^{13}$C NMR (CDCl$_3$, 300 MHz): δ = 121.2 (d, J = 5.0 Hz), 127.9, 128.0, 129.4, 136.5, 139.4 (p, J = 5.0 Hz), 140.9 (dd, J = 56.2, 28.3 Hz), 143.2 (p, J = 28.6 Hz), 149.3 (d, J = 15.2 Hz), 153.3, 156.6 |
| a3 | b1 | 3-(E)-2-Chloro-((2-phenylvinyl)tetrafluorosulfanyl)-2,6-difluoropyridine<br>c5 37% Yield<br>MS (EI, m/z) 359 (M+); $^1$H NMR (CDCl$_3$, 300 MHz): δ = 6.78 (d, J = 8.6 Hz, 1H), 7.17 (dquint, J = 8.9, 1.9 Hz, 1H), 7.37-7.45 (br, 5H), 8.20-8.05 (m, 1H); $^{19}$F NMR (CDCl$_3$, 300 MHz): δ = −66.3 (s, 1F), −61.2--61.8 (m, 1F), 73.4 (dd, J = 23.1, 8.9 Hz, 4F); $^{13}$C NMR (CDCl$_3$, 300 MHz): δ = 106.1 (dd, J = 35.6, 6.1 Hz), 127.9, 128.1, 129.4, 136.4, 138.5-137.1 (m), 139.7 (p, J = 7.7 Hz), 143.0 (p, J = 28.4 Hz), 144.4-143.8 (m), 153.8 (dd, J = 254.6, 15.3 Hz), 160.7 (dd, J = 251.6, 13.9 Hz) |
| a4 | b1 | 2,6-Dichloro-3-(E)-2-chloro-((2-phenylvinyl)tetrafluorosulfanyl)pyridine<br>c6 5% Yield<br>MS (EI, m/z) 391 (M+); $^1$H NMR (CDCl$_3$, 300 MHz): δ = 7.15 (quint, J = 8.4 Hz, 1H), 7.23 (d, J = 8.6 Hz, 1H), 7.45-7.36 (m, 5H), 7.99 (d, J = 8.6 Hz, 1H); $^{19}$F NMR (CDCl$_3$, 300 MHz): δ = 70.7 (d, J = 8.4 Hz, 4F); $^{13}$C NMR (CDCl$_3$, 300 MHz): δ = 122.5, 127.9, 128.1, 129.5, 136.4, 139.9-139.4 (m), 141.0 (p, J = 5.5 Hz), 143.1 (p, J = 28.3 Hz), 145.1-144.8 (m), 150.5, 153.6-152.3 (m) |

TABLE 1-continued

Example 1

| Source material | | |
|---|---|---|
| a1 | b4 | Vinyltetrafluorosulfanylpyridine |

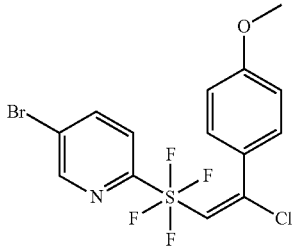 [SMILES: COc1ccc(/C(Cl)=C\S(F)(F)(F)(F)c2ccc(Br)cn2)cc1]

(E)-5-bromo-2-((2-chloro-2-(4-methoxyphenyl)vinyl)tetrafluorosulfanyl)pyridine
c7 71% Yield
MS (EI, m/z) 432 (M$^+$); $^1$H NMR (CDCl$_3$, 300 MHz): δ = 3.80 (s, 3H), 6.88 (d, J = 9.0 Hz, 2H), 7.17 (quint, J = 8.2 Hz, 1H), 7.38 (d, J = 8.7 Hz, 2H), 7.50 (d, J = 8.7 Hz, 1H), 7.88 (d, J = 8.4 Hz, 1H), 8.49 (s, 1H); $^{19}$F NMR (CDCl$_3$, 282 MHz): δ = 61.0 (d, J = 7.6 Hz, 4F)

| a1 | b5 | |

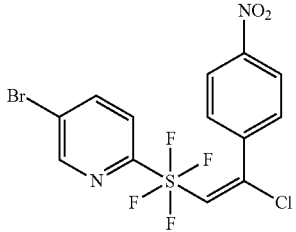 [SMILES: O=[N+]([O-])c1ccc(/C(Cl)=C\S(F)(F)(F)(F)c2ccc(Br)cn2)cc1]

(E)-5-bromo-2-((2-chloro-2-(4-nitrophenyl)vinyl)tetrafluorosulfanyl)pyridine
c8 51% Yield
MS (EI, m/z) 447 (M$^+$); $^1$H NMR (CDCl$_3$, 300 MHz): δ = 7.27 (quint, J = 8.1 Hz, 1H), 7.48 (d, J = 8.7 Hz, 1H), 7.61 (d, J = 8.4 Hz, 2H), 7.90 (d, J = 8.7 Hz, 1H), 8.25 (d, J = 9.0 Hz, 2H), 8.49 (s, 1H); $^{19}$F NMR (CDCl$_3$, 282 MHz): δ = 61.4 (d, J = 7.6 Hz, 4F)

| a1 | b6 | |

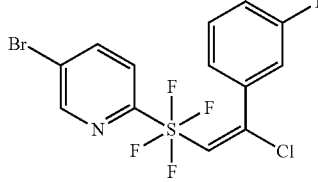

(E)-5-bromo-2-((2-chloro-2-(3-fluorophenyl)vinyl)tetrafluorosulfanyl)pyridine
c9 91% Yield
MS (EI, m/z) 419 (M$^+$); $^1$H NMR (CDCl$_3$, 300 MHz): δ = 7.08-7.02 (m, 1H), 7.26-7.13 (m, 3H), 7.37-7.30 (m, 1H), 7.48 (d, J = 8.7 Hz, 1H), 7.87 (d, J = 8.7 Hz, 1H), 8.49 (s, 1H); $^{19}$F NMR (CDCl$_3$, 282 MHz): δ = 61.2 (d, J = 7.6 Hz, 4F)

TABLE 1-continued

Example 1

| Source material | | |
|---|---|---|
| a1 | b7 | Vinyltetrafluorosulfanylpyridine |

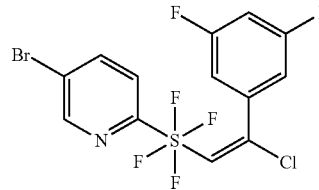

(E)-5-bromo-2-((2-chloro-2-(3,5-difluorophenyl)vinyl)tetrafluorosulfanyl)
c10 89% Yield
MS (EI, m/z) 437 (M$^+$); $^1$H NMR (CDCl$_3$, 300 MHz): δ = 6.84-6.72 (m, 1H), 6.97 (d, J = 5.1 Hz, 2H), 7.19 (quint, J = 8.2 Hz, 1H), 7.50 (d, J = 8.7 Hz, 1H), 7.89 (d, J = 8.4 Hz, 1H), 8.50 (s, 1H); $^{19}$F NMR (CDCl$_3$, 282 MHz): δ = −108.8−−109.2 (m, 2F), 61.3 (d, J = 9.3 Hz, 4F)

| a1 | b8 | |

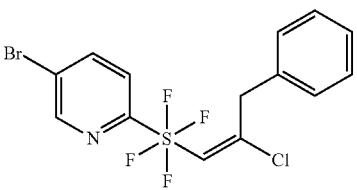 [SMILES: FS(F)(F)(F)(/C=C(/Cl)Cc1ccccc1)c1ccc(Br)cn1]

(E)-5-bromo-2-((2-chloro-3-phenylprop-1-en-1-yl)tetrafluorosulfanyl)pyridine
c11 20% Yield
MS (EI, m/z) 415 (M$^+$); $^1$H NMR (CDCl$_3$, 300 MHz): δ = 4.16 (s, 2H), 7.00 (t, J = 8.2 Hz, 1H), 7.31 (br, 5H), 7.68 (d, J = 8.4 Hz, 1H), 7.98 (d, J = 7.2 Hz, 1H), 8.59 (s, 1H); $^{19}$F NMR (CDCl$_3$, 282 MHz): δ = 59.8 (d, J = 7.6 Hz, 4F)

| a1 | b9 | |

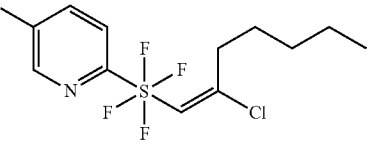

(E)-5-bromo-2-((2-chlorohept-1-en-1-yl)tetrafluorosulfanyl)pyridine
c12 90% Yield
MS (EI, m/z) 395 (M$^+$); $^1$H NMR (CDCl$_3$, 300 MHz): δ = 0.90 (s, 3H), 1.35 (br, 4H), 1.67 (s, 2H), 2.78 (t, J = 7.4 Hz, 2H), 6.85 (quint, J = 8.7 Hz, 1H), 7.64 (d, J = 9.0 Hz, 1H), 7.97 (d, J = 8.4 Hz, 1H), 8.58 (s, 1H); $^{19}$F NMR (CDCl$_3$, 282 MHz): δ = 59.2 (d, J = 7.6 Hz, 4F)

Example 2

The following reaction was performed to synthesize an alkyltetrafluorosulfanylpyridine compound (c′).

[Chemical Formula 10]

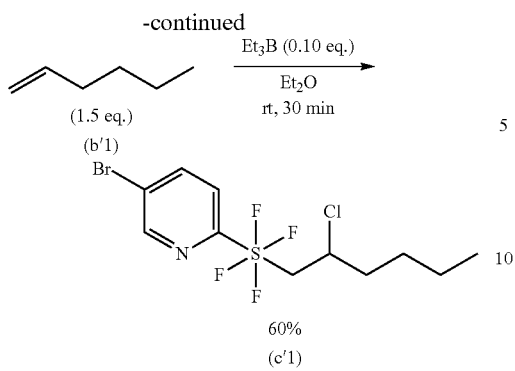

A 100 mL flask was charged with chlorotetrafluoropyridine (a1) (446 mg, 1.48 mmol) synthesized by the inventors, diethyl ether (3.7 mL), and 1-hexene (b'1) (0.28 mL, 2.2 mmol, manufactured by Wako Pure Chemical Industries, Ltd.) under a nitrogen atmosphere. Then, a triethylborane/hexane solution (0.15 mL, 1.0 M, manufactured by Sigma-Aldrich) was added to the mixture, and the mixture was stirred at room temperature for 30 minutes. After the end of the reaction, a saturated aqueous solution of sodium hydrogencarbonate was added, the product was extracted with dichloromethane, and the organic phase was dried over magnesium sulfate. Then, the solvent was distilled off under reduced pressure, and the mixture was purified by silica gel column chromatography (hexane/ethyl acetate=9/1, Rf value 0.37) to give product (c'1) (344.2 mg, 60%) as a white solid.

Furthermore, the same synthesis was performed using the following compounds. The results of analyses by mass spectrometry and NMR are collectively shown below.

[Chemical Formula 11]

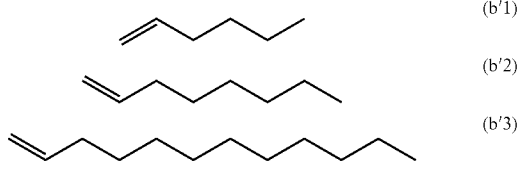

TABLE 2

| Source material | Example 2 Alkyltetrafluorosulfanylpyridine |
|---|---|
| a1  b'1 | 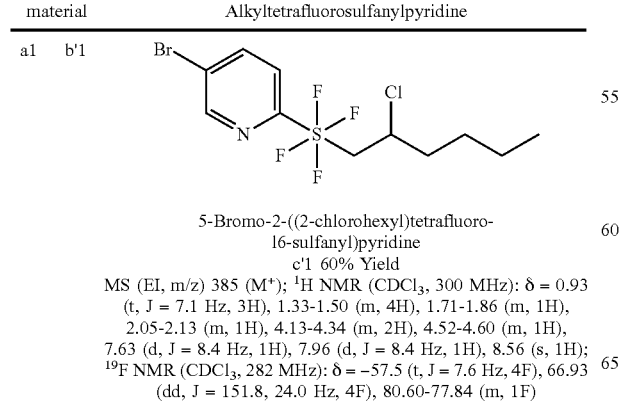 5-Bromo-2-((2-chlorohexyl)tetrafluoro-l6-sulfanyl)pyridine c'1 60% Yield MS (EI, m/z) 385 (M⁺); $^1$H NMR (CDCl$_3$, 300 MHz): δ = 0.93 (t, J = 7.1 Hz, 3H), 1.33-1.50 (m, 4H), 1.71-1.86 (m, 1H), 2.05-2.13 (m, 1H), 4.13-4.34 (m, 2H), 4.52-4.60 (m, 1H), 7.63 (d, J = 8.4 Hz, 1H), 7.96 (d, J = 8.4 Hz, 1H), 8.56 (s, 1H); $^{19}$F NMR (CDCl$_3$, 282 MHz): δ = −57.5 (t, J = 7.6 Hz, 4F), 66.93 (dd, J = 151.8, 24.0 Hz, 4F), 80.60-77.84 (m, 1F) |

TABLE 2-continued

| Source material | Example 2 Alkyltetrafluorosulfanylpyridine |
|---|---|
| a1  b'2 | 5-bromo-2-((2-chlorooctyl)tetrafluorosulfanyl)pyridine c'2 69% Yield MS (EI, m/z) 411 (M⁺); $^1$H NMR (CDCl$_3$, 300 MHz): δ = 0.87 (s, 3H), 1.43-1.30 (m, 8H), 1.86-1.73 (m, 1H), 2.14-2.03 (m, 1H), 4.38-4.13 (m, 2H), 4.60-4.52 (m, 1H), 7.62 (d, J = 8.7 Hz, 1H), 7.95 (d, J = 8.4 Hz, 1H), 8.55 (s, 1H); $^{19}$F NMR (CDCl$_3$, 282 MHz): δ = 57.6 (d, J = 7.6 Hz, 4F) |
| a1  b'3 | 5-bromo-2-((2-chlorododecyl)tetrafluorosulfanyl)pyridine c'3 71% Yield MS (EI, m/z) 467 (M⁺); $^1$H NMR (CDCl$_3$, 300 MHz): δ = 0.88 (s, 3H), 1.26 (br, 16H), 1.82-1.73 (m, 1H), 2.10-2.06 (m, 1H), 4.33-4.16 (m, 2H), 4.55 (s, 1H), 7.61 (d, J = 8.4 Hz, 1H), 7.95 (d, J = 8.4 Hz, 1H), 8.55 (s, 1H); $^{19}$F NMR (CDCl$_3$, 282 MHz): δ = 57.5 (d, J = 7.6 Hz, 4F) |

It is clear that pyridine having a tetrafluorosulfanyl group can be obtained by the present invention. Also, various compounds having a pyridine ring, with a tetrafluorosulfanyl group being as a linker, can be synthesized by the production method of the present invention. Accordingly, the present invention is useful for synthesizing novel functional materials and physiologically active substances such as pharmaceutical and agricultural chemicals.

The invention claimed is:

1. A tetrafluorosulfanylpyridine represented by the formula (c):

Chemical Formula (c)

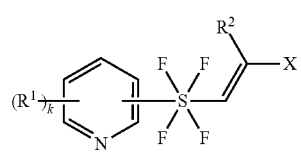

wherein
k is 1 or 2;
X is a hydrogen atom or a halogen atom;
$R^1$ is a hydrogen atom, a halogen atom, a substituted or unsubstituted alkyl group having 1 to 18 carbon atoms, a substituted or unsubstituted aryl group having 6 to 30 carbon atoms, or a nitro group; and
$R^2$ is a substituted or unsubstituted alkyl group having 1 to 18 carbon atoms or a substituted or unsubstituted aryl group having 6 to 30 carbon atoms.

2. The tetrafluorosulfanylpyridine according to claim 1, wherein $R^1$ is a fluorine atom or a chlorine atom, and X is a chlorine atom.

3. A tetrafluorosulfanylpyridine represented by the formula (c'):

Chemical Formula (c')

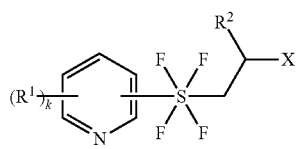

wherein k is 1 or 2;

X is a hydrogen atom or a halogen atom;

$R^1$ is a hydrogen atom, a halogen atom, a substituted or unsubstituted alkyl group having 1 to 18 carbon atoms, a substituted or unsubstituted aryl group having 6 to 30 carbon atoms, or a nitro group; and $R^2$ is a substituted or unsubstituted alkyl group having 1 to 18 carbon atoms or a substituted or unsubstituted aryl group having 6 to 30 carbon atoms.

4. The tetrafluorosulfanylpyridine according to claim 3, wherein $R^1$ is a fluorine atom or a chlorine atom, and X is a chlorine atom.

5. A method for producing the tetrafluorosulfanylpyridine according to claim 1, comprising the step of:

addition of a radical species generated from a halotetrafluoropyridine represented by the formula (a) to an alkyne represented by the formula (b) to give a tetrafluorosulfanylpyridine represented by the formula (c):

Chemical Formula (c)

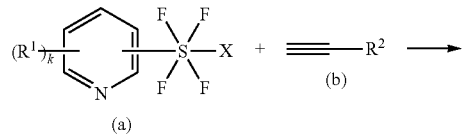

-continued

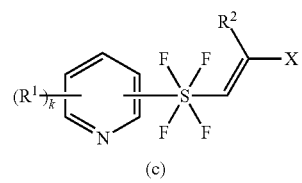

wherein $R^1$, $R^2$, X, and k are as defined above.

6. A method for producing the tetrafluorosulfanylpyridine according to claim 3, comprising the step of:

addition of a radical species generated from a halotetrafluoropyridine represented by the formula (a) to an alkene represented by the formula (b') to give a tetrafluorosulfanylpyridine represented by the formula (c'):

Chemical Formula (c')

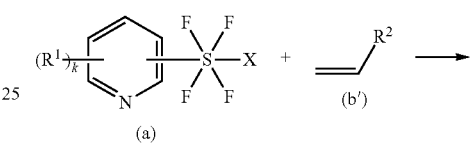

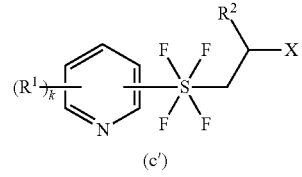

wherein $R^1$, $R^2$, X, and k are as defined above.

* * * * *